United States Patent [19]

Rovins

[11] 4,171,569
[45] Oct. 23, 1979

[54] DENTAL PIN

[75] Inventor: Morton Rovins, Merion, Pa.

[73] Assignee: Star Dental Manufacturing Co., Inc., Conshohocken, Pa.

[21] Appl. No.: 843,398

[22] Filed: Oct. 19, 1977

[51] Int. Cl.² ............................................. A61C 5/04
[52] U.S. Cl. ...................................................... 32/15
[58] Field of Search ............. 32/15, 6, 7, 10 A, 10 R; 145/50 R; 85/42, 41; D8/82, 387; 128/329 A

[56] References Cited

U.S. PATENT DOCUMENTS

| 71,909 | 12/1867 | Pierce | 85/42 |
|---|---|---|---|
| 686,424 | 11/1901 | Smith | 145/50 R |
| 1,294,268 | 2/1919 | Holmes | 85/41 |
| 3,861,043 | 1/1975 | Lieb et al. | 32/15 |
| 3,905,375 | 9/1975 | Toyama | 128/329 A |

Primary Examiner—Louis G. Mancene
Assistant Examiner—John J. Wilson
Attorney, Agent, or Firm—Tom M. Moran; Joseph I. Hirsch

[57] ABSTRACT

Novel dental pins having a first shaft, a handle secured to one end of the first shaft, and a second shaft connected to the handle at a point substantially directly opposite the attachment of the first shaft. Each shaft preferably has a roughened or uneven surface to improve the retention of that portion thereof which remains in a pre-drilled hole in a patient's tooth. Each shaft also has a fracture groove between the leading portion of the shaft and the handle so that the handle and the remaining portions of the shafts adjacent thereto can be separated from the leading portions which remain in the pre-drilled holes after insertion. Preferably, each shaft has a self-tapping flute at the leading edge thereof which cuts a thread into the dentine as the shaft is rotatably inserted therein.

18 Claims, 7 Drawing Figures

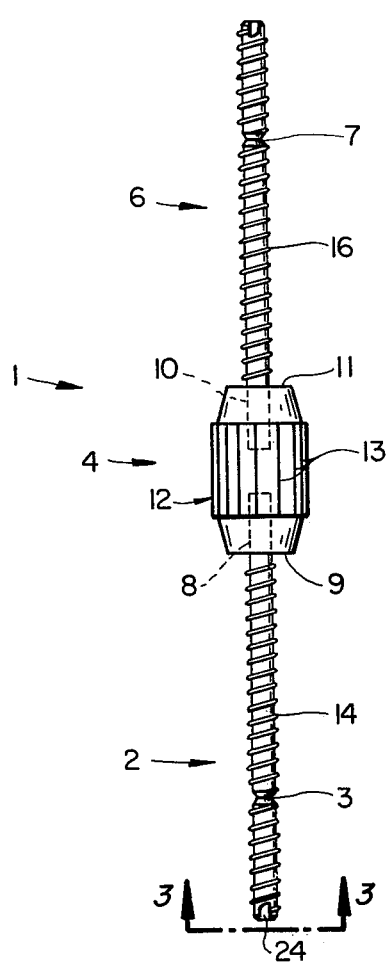
FIG_1
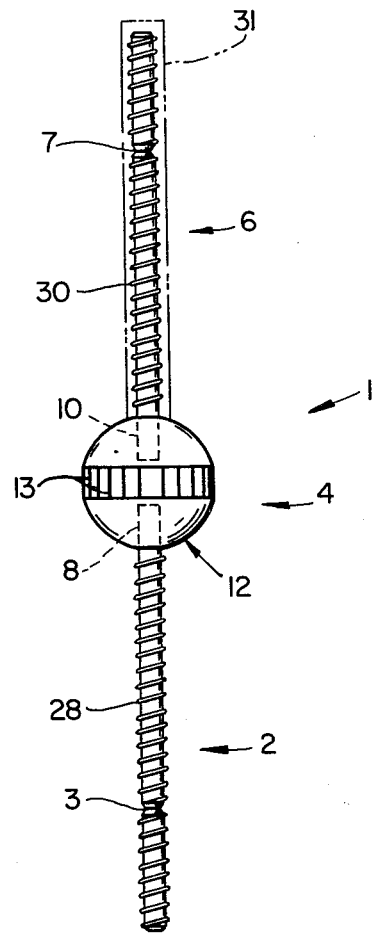
FIG_2
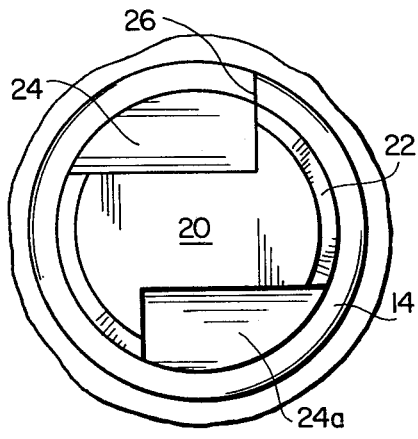
FIG_3
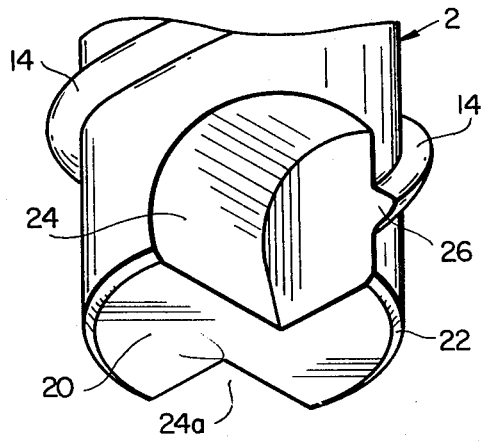
FIG_4

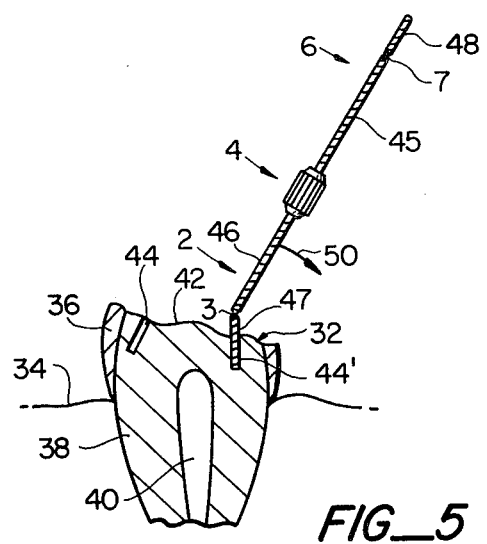
FIG_5
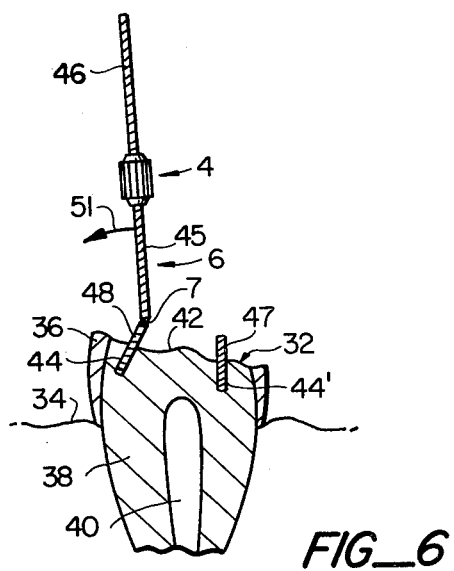
FIG_6
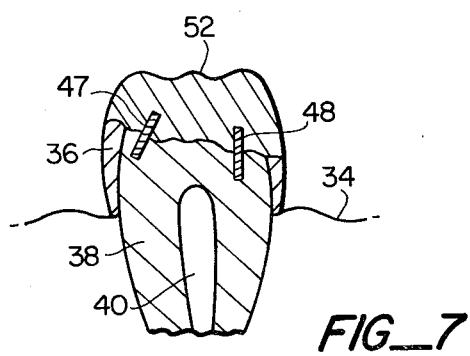
FIG_7

DENTAL PIN

BACKGROUND OF THE INVENTION

1. Field of the Invention

This invention relates to novel dental pins. More particularly, it relates to novel dental pins having a pair of shafts, one on each side of an intermediate handle of sufficient dimensions to be digitally grasped by the dentist. Each shaft has a fracture groove between the leading portion of the shaft and the handle so the leading portion can be severed from the handle after the shaft has been securely inserted into a pre-drilled hole in the patient's tooth.

2. Prior Art

It is generally known that dental pins can be used in building superstructures on a tooth having a substantial portion thereof that has been removed.

The dental pin disclosed in U.S. Pat. No. 3,928,915 has no handle but has a plurality of threaded sections which are connected by regions of reduced cross-section.

Another dental pin which requires a wrench is disclosed in U.S. Pat. No. 3,675,328 to Weissman. This patent discloses a plurality of self-threading sections which are separated from each other by a fracture groove so that the leading section can be easily separated from the next adjacent after the leading section has been screwed into a pre-drilled hole in a tooth.

A self-tapping, one-use dental pin having an integral handle and a self-tapping flute at its leading edge is disclosed in U.S. Pat. No. 3,861,043 to Lieb et al.

OBJECTS OF THE INVENTION

It is an object of this invention to provide a novel dental pin.

It is a further object of this invention to provide a novel dental pin which can be used twice.

It is a further object to provide a novel dental pin having two separate detachable shaft portions, one each for insertion into separate pre-drilled holes.

SUMMARY OF THE INVENTION

These and other objects of the invention are accomplished by providing a dental pin which comprises
a first shaft;
a handle which (i) has a dimension transverse to the axis of the first shaft which is substantially larger than the diameter of the first shaft, (ii) is attached to one end of the first shaft and (iii) has a surface which can be digitally grasped by the dentist during use; and
a second shaft of smaller diameter than the handle and being attached to the handle at a point substantially directly opposite the attachment of the first shaft.

The first and second shafts each have a fracture groove of reduced thickness located between the leading edge of each shaft and its attachment to the handle and a roughened or uneven surface at least between the fracture groove and the leading edge of each shaft. Preferably, at least one of the shafts has a continuous helical thread extending around the length of the shaft, and even more preferably the two shafts are of equal length and diameter and each has a helical thread extending substantially along the entire length of the shaft.

Optimally, at least one of the shafts, and preferably both, has (have), at the unattached end, means for tapping a thread in a tooth as the pin is being inserted into a pre-drilled hole. This is accomplished by providing at least one cutting face, or flute, and preferably two, at an unattached end.

BRIEF DESCRIPTION OF THE DRAWINGS

FIG. 1 is a front elevational view, showing the dental pin of this invention.

FIG. 2 is a schematic view of another embodiment of the dental pin of this invention.

FIG. 3 is a bottom plan view of the dental pin of FIG. 1 taken along lines 3—3.

FIG. 4 is an enlarged perspective view of the leading edge of the dental pin of FIG. 1.

FIG. 5 is a sectional view of a tooth showing initial or partial use of the dental pin of this invention.

FIG. 6 is a sectional view of the same tooth showing the remaining use of the dental pin of this invention.

FIG. 7 is a sectional view of a tooth that has been reconstructed using the two shafts of the dental pin of this invention.

DESCRIPTION OF THE INVENTION AND PREFERRED EMBODIMENT

Referring now in greater detail to the various Figures of the drawings wherein the reference characters refer to like parts, a dental pin 1 embodying the present invention is shown in FIGS. 1 and 2. Dental pin 1 basically comprises a first shaft 2, a handle 4 which is integral with the shaft and a second shaft 6 which is attached to the handle at a point substantially directly opposite the attachment of the first shaft.

As seen in FIG. 1, shafts 2 and 6 have uneven, i.e., roughened, external surfaces as exemplified by continuous helical threads 14 and 16 (and 28 and 30 in FIG. 2) extending longitudinally around the respective surface of each shaft. Alternatively, this roughened or uneven external surface can be achieved by providing annular rings, knurls or scorings on the shaft. Even the use of square stock rather than round stock in the manufacturing of the shaft and rolling, machining or stamping threads or scorings onto the shaft surface can be used. Although shaft 2 and shaft 6 may be of different cross-sectional shapes and diameters, preferably they are cylinders of substantially the same diameter and length.

Shaft 2 has a fracture groove 3 of reduced cross-sectional area intermediate the leading end of shaft 2 and bore 8 in handle 4 into which the other end of the shaft is inserted, while shaft 6 includes fracture groove 7 of reduced cross-sectional area intermediate its leading end and bore 10 in handle 4 into which the other end of shaft 6 is inserted.

The helical thread extending around the length of the shaft can have a sharpened outer edge which permits the pin to be self-threading. That is, the sharpened edge actually wedges into the dentine of the tooth so as to help retain the pin in the hole that is drilled by the dentist. Preferably, however, the helical thread has a rounded or arcuate outer edge as shown, for example, in FIG. 4. Helical threads 14 and 16 extend from the respective unattached ends of shafts 2 and 6 to the fracture grooves 3 and 5 and may extend substantially the entire length of each of shaft 2 and 6 if so desired.

The handle 4 has a gripping surface 12 which preferably is roughened or knurled to provide the proper friction so that the handle can be readily held between the thumb and forefinger by the dentist. The roughened surface can be prepared, for example, by merely cutting or forming longitudinal grooves 13 in the circumferential surface of the handle. Although the handle may be of any cross-sectional shape such as rectangular, triangular, circular, or substantially spherical (as shown in FIG. 2 hereof), it preferably is substantially cylindrical as shown in FIG. 1. The handle 4 has two faces 9 and 11 to which shafts 2 and 6 are respectively attached. It is seen that the handle 4 has a transverse dimension (i.e., transverse to the axis of the shafts) that is substantially larger, about 4-8 times (e.g. about 5 times), than the diameter of the shafts. The handle has internal bores 8 and 10 for the receipt of shafts 2 and 6, respectively, which can be satisfactorily secured within the bores by a pressed fit. If desired, the handle can additionally be secured in place by screwing or passing pins through the handle and each of shafts 2 and 6.

In the embodiment shown in FIG. 1, shafts 2 and 6 are threaded only up to handle 4, and are smooth on their outer surface from that point on. If desired, the shafts can be formed from threaded stock as shown in FIG. 4, and the threaded portion will project into the handle. Dental pin 1 will carry out its intended function, regardless of whether the threads extend into the handle or only between the fracture groove and the leading edge of the shaft.

The dental pin 1 of FIG. 2 is similar to the pin of FIG. 1, except that the threads are designated as 28 and 30 and the handle is substantially spherical.

As shown in FIG. 2 a protective sheath 31 can fit over one or both shafts during storage to protect the shaft from inadvertent breakage or other damage.

Referring now to FIGS. 3 and 4, it can be seen that the bottom 20 of shaft 2, shown in FIG. 1, is flat, and includes a small beveled edge 22. Two cuts are made in the bottom face of shaft 2 forming slots 24 and 24a. The slots can be formed by any means known to the art, such as an end mill or a file. A plurality of cutting edges may be obtained by providing tapping flutes on threaded shaft. When the slots are cut, sharp leading edges 26 are formed on thread 14. If desired, only a single slot 24 with a single leading edge 26 on thread 14 can be formed on either or both shafts, these slots or flutes provide a self-tapping leading edge in the manner described in U.S. Pat. No. 3,861,043.

The dental pin of this invention is used in the same manner as the dental pin of U.S. Pat. No. 3,861,043. Thus, the pin is used in the reconstruction of a severely decayed or damaged tooth, which is generally shown at 32 in FIGS. 5-7. The tooth is in the soft tissue or gingiva 34 of the human gum. The tooth includes the enamel 36 which covers the dentine 38. The dentine in turn encloses a pulp channel 40. Prior to reconstructing the tooth, a portion of the enamel and a portion of the dentine are excavated in order to remove decayed and undermined understructure, thereby forming the excavated surface 42, which is free of decay.

In order to build a superstructure on the remaining portion of tooth 32, the first step in using the dental pin of this invention is to drill a plurality of holes 44, 44' into the dentine. These holes have a diameter which is slightly smaller than the outer diameter of the threads 14 and 16 of pin 1. The difference in diameter is on the order of 0.002 to 0.003 inch. Thereafter, shaft 2 of dental pin 1 is threaded into hole 44' and shaft 6 is threaded into hole 44. This is accomplished by placing the leading edge of shaft 2 adjacent the entrance to hole 44 and rotating handle 4 between the thumb and forefinger. As this is done, sharp leading edge 26 of thread 14 adjacent slot 24 actually cuts a helical path through the dentine, and the remainder of the pin is threaded along this path by applying a rotational force on the handle and a slight downward pressure against the tooth.

After the pin has reached its desired depth, which is determined by the depth of the pre-drilled hole, handle 4, shaft 6, and the upper portion 46 of shaft 2 are removed by bending shaft 2 at fracture groove 3, which is easily accomplished once the leading portion 47 of shaft 2 is firmly secured within the hole. Thus, the fracture groove is sufficiently strong to take the torque or twisting motion it receives upon insertion of the shaft, but is sufficiently weak so as to break when an increased torsional force or bending is applied to the fracture groove, as shown by the arrow 50 in FIG. 5. Generally, the increased torsional force is applied after the pin reaches the bottom of the pre-drilled hole. By following a similar procedure and applying force in the direction of arrow 51 or increased torsional force, the leading portion 48 of shaft 6 is threaded into hole 44 and then severed along fracture groove 7. Handle 4 with attached portions 45 and 46 of shafts 6 and 2, respectively, is then discarded.

Leading portions 47 and 48 of shafts 2 and 6, respectively, serve as anchors for building a superstructure on the excavated tooth. As seen in FIG. 7, anchors 47 and 48 are in a non-parallel relationship to each other, although it is not essential that they be so positioned. The number of anchors used can vary, depending on the size of the tooth and the amount of the superstructure that is to be built thereon. Once anchors 47 and 48 are in place, the superstructure 52 is built on the exposed excavated surface 42. Any material known to the art can be useful for the superstructure. By way of example, the superstructure can be silver restoration material or a self-curing resin.

The superstructure 52 is retained on the exposed portions of anchors 47 and 48. The threads on the shafts aid in the retention of the superstructure, as does the angular relationship between the anchors. Thus, the firmly threaded anchors serve to anchor the superstructure in position and reinforce its retention to surface 42.

Alternatively, the dental pin may, as mentioned previously, be of the self-threading type instead of the self-tapping type which has been explained in detail with regard to FIGS. 3-7 above.

In keeping with this invention, the dental pin may also have annular rings, knurls or scorings on the surface instead of the continuous helical thread shown in FIGS. 1 and 2, and the pin may be used in conjuction with a suitable cement such as the cyanoacrylic cement of U.S. Pat. No. 3,928,915 to retain the pins in the pre-drilled holes. The adhesion strength of the pin to the cement is improved by roughening the pin surface forming crevices in which the cement can lodge and impede pull-out or rotation of the pin. In this embodiment, one can use square stock rather than round stock in the manufacture of the pins, followed by rolling, machining or stamping threads, rings, knurls, or scorings in the pin surface. The traverse recesses formed when filled with cement resist pull-out of the pin from the hole in which it is placed, while the longitudinal recesses formed by the flat sides of the pin, between the square corners, when filled with cement resist pin rotation.

Referring again to FIGS. 5-7, in use of the dental pin of this invention with cement, the dentist first drills the desired number of holes in the tooth to receive the leading shaft portions. Then, holding handle 4 of dental pin 1, he places some cement in the first hole or applies a thin layer of cyanoacrylate cement to the leading portion 47 of shaft 2 and quickly inserts the coated shaft into the drilled hole. After the cement hardens, the pin is locked in place. The dentist then breaks off section 47 at fracture groove 3, applies a new coat of cement to the next hole or to the leading portion 48 of shaft 6, and inserts the coated end into the second hole. He then breaks off leading portion 48 at fracture groove 7, and discards the handle with attached shaft portions.

It is thus seen that the dental pins of this invention are used in the same manner as the dental pins in the prior art, as exemplified by the patents cited above. The pins can be used in a non-parallel relationship to each other on the tooth in order to ensure better anchoring of the superstructure which is built over the pins. The provision of the integral handle or head 4 greatly facilitates the use of the pins of this invention. Initially, provision of the handle facilitates the picking up of a pin for use. The shafts of the pins are extremely small in diameter, with the major diameter (between opposing crests of thread) being on the order of 0.028 inch, and are accordingly most difficult to handle. However, by providing the intergral handle which can have a diameter of, for example, five times the diameter of the pin, it is much easier to manipulate the pins and pick them up for use. Additionally, there is no need to releasably secure a wrench to the small pins when it is desired to insert the pins in the pre-drilled holes. Instead, handle 4 is digitally manipulated so as to insert the pins in place.

The principal advantage of the dental pin of this invention, however, is the provision of two shafts on one handle to give two anchors without having to pick up a second pin.

The self-tapping cutting edge of the preferred embodiment hereof exhibits the advantage of shearing the dentine when the pin is inserted, and tapping a threaded hole for the pin. Contrasted with this, the self-threading pins act by wedging the threads into the dentine as the pin is inserted. This results in a constant force on the tooth, and can cause the tooth to crack or form hairline fractures unless great care is taken. These disadvantages are avoided by utilizing a pin having a self-tapping edge as described herein and in Lieb et al U.S. Pat. No. 3,861,043.

The pins of this invention can be made in any size that are used for the prior art pins or in any sizes which are readily adaptable for use in a given tooth. By way of non-limiting example, the pins of this invention can have an overall length of about 23 mm. The major diameter of the pins across the threads is 0.028 inch and the threads have a height of 0.0035 inch. The fracture grooves are approximately 4.5 mm from the leading edge of each shaft, and have a diameter of about 0.018 inch. Of course, it is to be understood, that the foregoing dimensions are solely by way of example, and obviously can be varied to suit the needs for any given tooth or operative procedure.

The pins can be made from any material known to the art. By way of example, stainless steel is preferred material. If desired, the pins can also be given a gold-plated surface.

Thus it is apparent that there has been provided, in accordance with the invention, a dental pin that fully satisfies the objects, aims, and advantages set forth above. While the invention has been described in conjunction with specific embodiments thereof, it is evident that other alternatives, modifications, and variations will be apparent to those skilled in the art in light of the foregoing description. Accordingly, it is intended to embrace all such alternatives, modifications, and variations as fall with the spirit and broad scope of the appended claims.

What is claimed is:

1. A dental pin which comprises
    a first shaft;
    a handle which (i) has a dimension transverse to the axis of said first shaft which is substantially larger than the widest cross-sectional dimension of said first shaft, (ii) is attached to one end of said first shaft, and (iii) has a gripping surface which can be easily grasped during use; and
    a second shaft of smaller cross-sectional dimension than said handle, said second shaft being attached to said handle at a point substantially directly opposite the attachment of said first shaft;
    said first and second shafts each having a fracture groove of reduced thickness located between the end of each respective shaft and said handle and an uneven external surface between the fracture groove and free end of each respective shaft.

2. The dental pin of claim 1 wherein at least one of said shafts has a continuous helical thread extending substantially along the entire length of said shaft.

3. The dental pin of claim 2 wherein the other of said shafts has a continuous helical thread extending substantially along the entire length of said shaft, and both of said shafts are of substantially equal length and diameter.

4. The dental pin of claim 1 wherein said handle is of substantially cylindrical configuration having a roughened gripping circumferential surface and first and second parallel end faces, said first shaft being attached to the center of said first face and said second shaft being attached to the center of said second face.

5. The dental pin of claim 1 wherein at least one of said shafts has a protective cover thereon.

6. A dental pin which comprises
    a cylindrical first shaft;
    a handle which (i) has a dimension transverse to the axis of said first shaft which is substantially larger than the diameter of said first shaft, (ii) is attached to one end of said first shaft and (iii) has an external gripping surface which can be easily grasped during use of said pin; and
    a second cylindrical shaft of smaller diameter than said handle, said second shaft being attached to said handle substantially directly opposite the attachment of said first shaft;
    said first and second shafts each having a fracture groove of reduced thickness located between the end of each respective shaft and said handle and a helical thread extending between said fracture groove and free end of each respective shaft.

7. The dental pin of claim 6 wherein at least one of said shafts has a protective cover thereon.

8. The dental pin of claim 6 wherein said handle is of substantially cylindrical configuration having a roughened gripping circumferential surface and first and second parallel end faces, said first shaft being attached to the center of said first face and said second shaft being attached to the center of said second face.

9. The dental pin of claim 6 wherein both of said shafts are of substantially equal length and diameter.

10. The dental pin of claim 6 wherein at least one of said shafts has means on said shaft for tapping a thread in a tooth.

11. The dental pin of claim 10 wherein said tapping means comprises at least one cutting face formed on the leading edge of the helical thread at the unattached end of said shaft.

12. The dental pin of claim 11 wherein said tapping means comprises a plurality of cutting faces.

13. The dental pin of claim 12 wherein said tapping means comprises two cutting faces.

14. The dental pin of claim 11 wherein said cutting face is defined by a flute formed at the unattached end of said shaft.

15. The dental pin of claim 10 wherein the other of said shafts has means therein for tapping a thread in a tooth, said tapping means comprising at least one cutting face formed on the leading edge of the helical thread at the unattached end of said other shaft.

16. The dental pin of claim 15 wherein said cutting faces are defined by flutes formed at the respective unattached ends of said shafts.

17. The dental pin of claim 16 wherein said tapping means comprises a plurality of cutting faces.

18. The dental pin of claim 17 wherein said tapping means comprises two cutting faces.

* * * * *